US010596350B2

(12) United States Patent
Kyvik

(10) Patent No.: US 10,596,350 B2
(45) Date of Patent: Mar. 24, 2020

(54) CATHETER SECUREMENT DEVICE WITH DUAL RETENTION STRAPS

(71) Applicant: Kurt T. Kyvik, Satellite Beach, FL (US)

(72) Inventor: Kurt T. Kyvik, Satellite Beach, FL (US)

(73) Assignee: KT KYUIK, LLC, Satellite Beach, FL (US)

( * ) Notice: Subject to any disclaimer, the term of this patent is extended or adjusted under 35 U.S.C. 154(b) by 233 days.

(21) Appl. No.: 15/833,571

(22) Filed: Dec. 6, 2017

(65) Prior Publication Data

US 2018/0154118 A1    Jun. 7, 2018

Related U.S. Application Data

(60) Provisional application No. 62/431,080, filed on Dec. 7, 2016.

(51) Int. Cl.
*A61M 25/02*    (2006.01)

(52) U.S. Cl.
CPC ..... *A61M 25/02* (2013.01); *A61M 2025/0253* (2013.01); *A61M 2025/0266* (2013.01); *A61M 2025/0273* (2013.01)

(58) Field of Classification Search
CPC .......... A61M 25/02; A61M 2025/0253; A61M 2025/0266; A61M 2025/0273
See application file for complete search history.

(56) References Cited

U.S. PATENT DOCUMENTS

| | | | | |
|---|---|---|---|---|
| 4,490,141 A | * | 12/1984 | Lacko | A61M 25/02 128/879 |
| D302,041 S | * | 7/1989 | Gentelia | D24/128 |
| 5,304,146 A | * | 4/1994 | Johnson | A61M 25/02 128/DIG. 26 |
| 7,524,307 B2 | * | 4/2009 | Davis | A61M 25/02 128/DIG. 26 |
| 2016/0206857 A1 | * | 7/2016 | Mitchell | A61M 25/02 |

* cited by examiner

*Primary Examiner* — Laura A Bouchelle
(74) *Attorney, Agent, or Firm* — Thomas C. Saitta

(57) ABSTRACT

A catheter securement device having a biocompatible, preferably anti-microbial, adhesively-backed main body, a mounting body affixed to the upper side of the main body, and a pair of retention strap members extending preferably substantially parallel to each other from the mounting body, the retention strap members joined to the mounting body along angled fold lines, such that the retention strap members overlap when folded along the fold lines. An adhesive layer is provided on the mounting body and the retention strap members which adheres to a catheter when the catheter is positioned on the mounting body and the retention strap members are folded across the catheter.

20 Claims, 4 Drawing Sheets

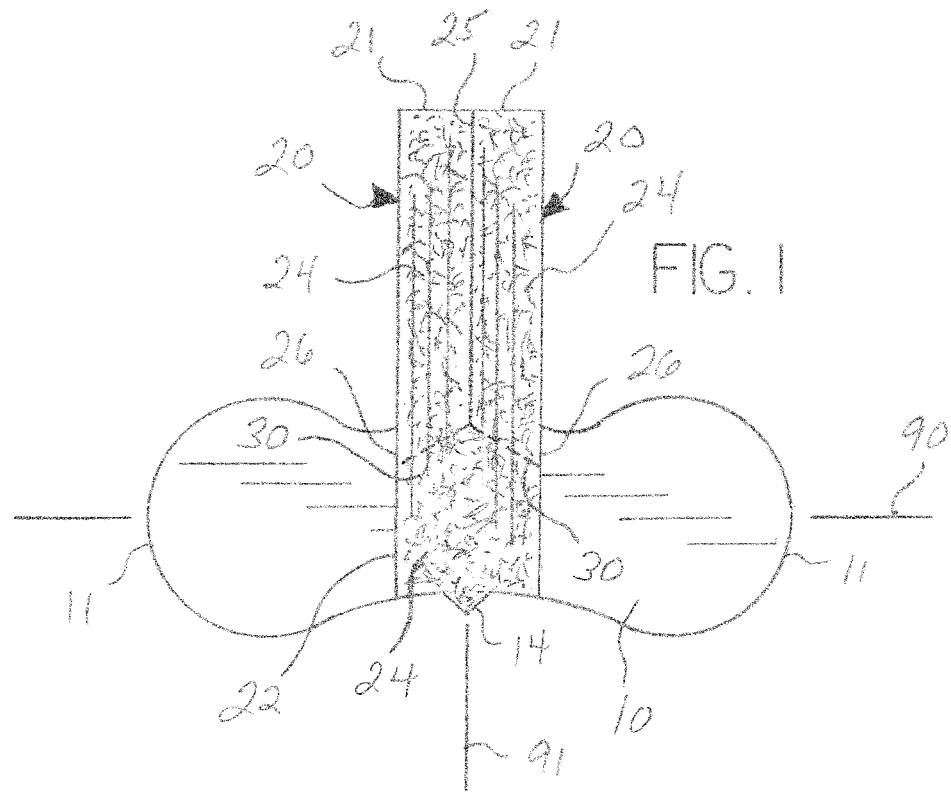
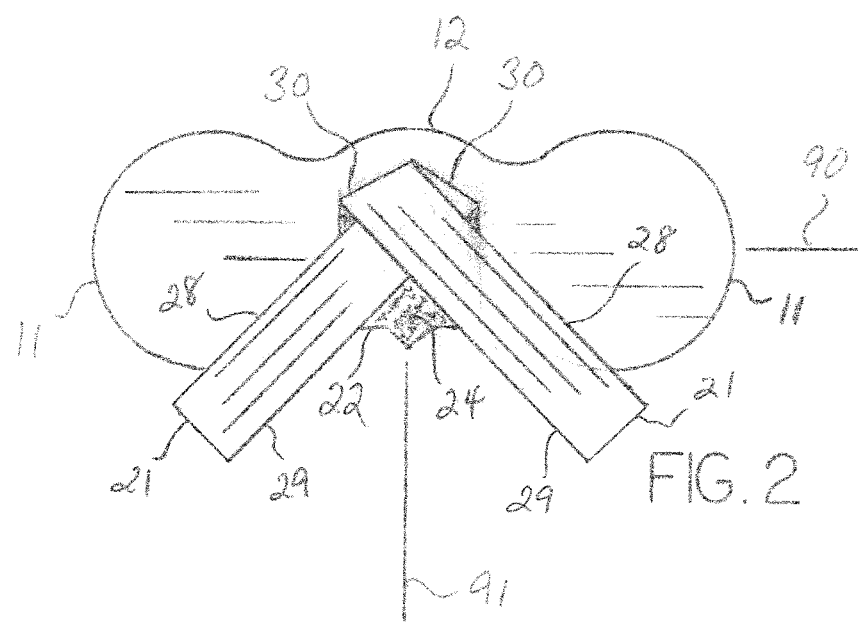

CATHETER SECUREMENT DEVICE WITH DUAL RETENTION STRAPS

BACKGROUND OF THE INVENTION

This invention relates generally to the field of medical devices referred to as catheter securement devices, a catheter being defined herein to include a small diameter, flexible tube that is inserted through a person's skin and into a vein to deliver or remove fluids such as blood, saline solutions, medications, etc., as well as a housing, coupling, manifold, junction or the like to which the tubing is connected. For example, the catheter may be part of an intra-venous (IV) system.

A catheter securement device typically comprises a flexible sheet member adhesively adhered to the patient's skin, the devices having a base member that overlays the catheter, or having structures that overlap or encircle the catheter. The catheter securement device secures the catheter in a relatively stable manner such that it is less likely for the catheter to be accidentally dislodged from the patient.

It is an object of this invention to provide a catheter securement device having an improved design and structure to better secure a catheter tube, the device being provided with a pair of substantially parallel retention strap members affixed to a base member in a manner whereby a fold line is defined for each retention strap member, the fold lines being oriented non-perpendicularly to the transverse axis of the main body, such that the strap members when folded extend across the transverse axis, overlap the catheter, and cross each other. The retention strap members being of sufficient length so as to be adhered to the base member and preferably the skin of the patient beyond the edge of the main body.

SUMMARY OF THE INVENTION

The invention as shown in various embodiments is a catheter securement device with dual retention straps, the catheter securement device designed and adapted to retain, restrain and secure a catheter to a fixed location on a patient, the catheter securement device being adhesively mounted to the skin of the patient.

The catheter securement device comprises a main body composed of a flexible, adhesive-backed sheet material defining a sufficiently wide footprint such that the main body resists accidental dislodgment or separation from the skin. The main body defines a longitudinal axis and a transverse axis, the main or longitudinal axis of the catheter being oriented along the transverse axis when secured to the device so as to be substantially perpendicular to the longitudinal axis of the main body. A pair of retention strap members, with each of the retention strap member most preferably parallel or substantially parallel to each other, extends from a mounting base positioned on the main body in the transverse direction, each strap member and the mounting base having an adhesive upper surface layer. The adhesive layers are covered with removable release liners prior to affixation of the main body to the patient and prior to affixation of the retention strap members to the catheter.

A linear junction or fold line is defined between each retention strap member and the mounting base, the mounting base being coextensively adhered to the main body while the retention strap members are not. The linear junction or fold line of each retention strap member is angled relative to the transverse and longitudinal axes, i.e., is non-perpendicular and non-parallel to the transverse and longitudinal axes, such that when a retention strap member is folded back toward the mounting base in order to secure a catheter positioned along the transverse axis, the retention strap member extends across the transverse axis to the other side of the catheter.

In alternative language, the invention in various embodiments may be described as a catheter securement device comprising a main body, a mounting body affixed to said main body, and retention strap members in an unfolded configuration extending from said mounting body; said main body having an adhesive underside, said main body defining a transverse axis and a longitudinal axis perpendicular to said transverse axis, said transverse axis being disposed between said retention strap members; said retention strap members each having a free end; said mounting body and said retention strap members having adhesive upper surfaces; whereby the junction of each of said retention strap members with said mounting body defines a fold line, such that said fold line is non-parallel and non-perpendicular to both said transverse axis and said longitudinal axis; whereby with said retention strap members folded toward said mounting body along said fold lines, said retention strap members extend across said transverse axis. Furthermore, such a device wherein said retention strap members are separated by a slit; wherein said retention strap members are separated by a gap; wherein said retention strap members extend substantially parallel to each other and to said transverse axis in the unfolded state; wherein the combination of said fold lines define an angle facing away from said free ends of said retention strap members in the unfolded configuration of less than 180 degrees; wherein the combination of said fold lines define an obtuse angle facing away from said free ends of said retention strap members in the unfolded configuration; wherein the combination of said fold lines define an angle facing away from said free ends of said retention strap members in the unfolded configuration between approximately 110 and 130 degrees; wherein said main body further comprises a transverse extension; wherein said main body further comprises an alignment guide member; and/or wherein with a catheter positioned atop said main body and said mounting body along said transverse axis, said catheter is secured by said adhesive upper surface of said mounting body and said adhesive upper surfaces of said retention strap members, said retention strap members being folded across said catheter.

Alternatively still, the invention in various embodiments may be described as a catheter securement device comprising a main body, a mounting body affixed to said main body, and retention strap members extending from said mounting body; said main body having an adhesive underside, said main body defining a transverse axis and a longitudinal axis perpendicular to said transverse axis; said retention strap members extending substantially parallel to each other and to said transverse axis in an unfolded state, with said transverse axis disposed between said retention strap members, each said retention strap member having a free end, an inside edge and an outside edge, wherein for each said retention strap member, said inside edge is shorter than said outside edge; said mounting body and said retention strap members having adhesive upper surfaces; whereby the junction of each of said retention strap members with said mounting body defines a fold line, such that each said fold line is non-perpendicular to said inside edge and said outside edge of each retention strap member; whereby with said retention strap members folded toward said mounting body along said fold lines, said retention strap members extend across said transverse axis. Furthermore, such a device wherein said retention strap members are separated by a slit;

wherein said retention strap members are separated by a gap; wherein the combination of said fold lines define an angle facing away from said free ends of said retention strap members in the unfolded configuration of less than 180 degrees; wherein the combination of said fold lines define an obtuse angle facing away from said free ends of said retention strap members in the unfolded configuration; and/or wherein the combination of said fold lines define an angle facing away from said free ends of said retention strap members in the unfolded configuration between approximately 110 and 130 degrees.

Alternatively still, the invention in various embodiments may be described as a catheter securement device comprising a main body, a mounting body affixed to said main body, and retention strap members extending from said mounting body; said main body having an adhesive underside, said main body defining a transverse axis and a longitudinal axis perpendicular to said transverse axis; said retention strap members extending substantially parallel to each other and to said transverse axis in an unfolded state, with said transverse axis disposed between said retention strap members, each said retention strap member having a free end, an inside edge and an outside edge, wherein for each said retention strap member, said inside edge is shorter than said outside edge; said mounting body and said retention strap members having adhesive upper surfaces; whereby the junction of each of said retention strap members with said mounting body defines a fold line, such that the combination of each said fold line and said shorter inside edge of each said retention strap member defines an obtuse angle and the combination of each said fold line and said outside edge of each retention strap member defines an acute angle; whereby with said retention strap members folded toward said mounting body along said fold lines, said retention strap members extend across said transverse axis. Furthermore, such a device wherein said retention strap members are separated by a slit; wherein said retention strap members are separated by a gap; wherein the combination of said fold lines define an angle facing away from said free ends of said retention strap members in the unfolded configuration of less than 180 degrees; wherein the combination of said fold lines define an obtuse angle facing away from said free ends of said retention strap members in the unfolded configuration; and/or wherein the combination of said fold lines define an angle facing away from said free ends of said retention strap members in the unfolded configuration between approximately 110 and 130 degrees.

BRIEF DESCRIPTION OF THE DRAWINGS

FIG. 1 is an illustration of a first embodiment of the catheter securement device, shown with the retention strap members in the unfolded position.

FIG. 2 is an illustration showing the embodiment of FIG. 1 with the retention strap members in the folded position.

DETAILED DESCRIPTION OF THE INVENTION

Figure 3:
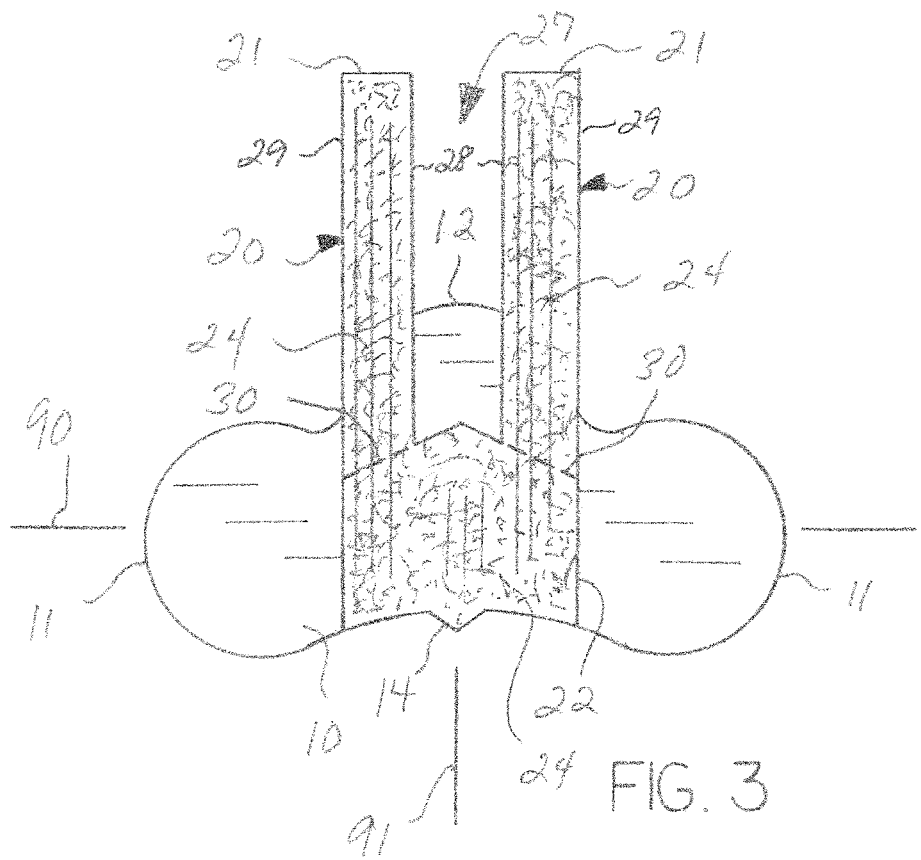
FIG. 3 is an illustration of a second embodiment of the catheter securement device, wherein the retention strap members are non-abutting.

With reference to the drawings and photographs, embodiments of the catheter securement device will now be described in detail, the illustrated embodiments intended to be non-limiting. In a broad sense, the catheter securement device comprises an adhesively-backed main body 10 defining a longitudinal axis 90 and a transverse axis 91 perpendicular to the longitudinal axis 90, wherein the catheter 100 is positioned and oriented along the transverse axis when retained by the overlapping retention strap members 20 of the catheter securement device. The term "catheter" as used herein shall be taken to include the catheter tube 101 and catheter housing 102. The term "catheter housing" shall be taken herein to refer to a housing, junction, connection, manifold, hub or the like to which one or more catheter tubes 101 are mounted to or retained by.

In one embodiment, as shown in FIGS. 1 and 2, the catheter securement device comprises an adhesively-backed, sheet-like, main body 10 having ends 11, wherein the adhesive is present on the bottom or underside of the main body 10 to secure the main body 10 to the skin 103 of a patient. The main body 10 defines a longitudinal axis 90 extending between the ends 11 and a transverse axis 91 extending perpendicular to the longitudinal axis 90, the transverse axis being preferably centrally located between the ends 11. The main body 10 is composed of a flexible, biocompatible sheet material. The adhesive disposed on the underside of the main body 10 is a biocompatible, preferably anti-microbial, adhesive suitable for use in securing the main body 10 to the skin of a patient, such adhesives being well known in the art, such as for example an adhesive which contains chlorhexidine or other antimicrobial ingredients. The main body 10 may further comprise a transverse extension 12 to increase the main body dimension in the transverse direction and to increase the contact footprint. The main body 10 may also comprise an alignment guide member 14, such as a projection from the main body 10, centered on the transverse axis 91 to provide a visual indication for the proper position of the catheter 100 by the medical practitioner.

A sheet-like mounting body 22 is affixed to the upper side of the main body 10 utilizing an adhesive, stitching, heat bonding or any other suitable mechanism. In this embodiment, the longer dimension of the mounting body 22 extends in the transverse direction, but as shown in other embodiments, the configuration and dimensions of the mounting body 22 may vary. A pair of retention strap members 20 extend from the mounting body 10 in the transverse direction, preferably substantially parallel to the transverse axis and substantially in parallel to each other, as shown in FIGS. 1 through 5, although the retention strap members 20 may angle apart from each other to form an angle of up to 45 degrees, as shown in FIG. 6, with the transverse axis 91 disposed between the two retention strap members 20. The retention strap members 20 are preferably of sufficient length to extend beyond the main body 10. The retention strap members 20 and the mounting body 22 are composed of a flexible, biocompatible sheet material, and may be composed of the same material as the main body 10. In this embodiment, the two retention strap members 20 may be defined by a slit 25 extending along the transverse axis. The mounting body 22 and the retention strap members 20 are most preferably folioed from a single sheet of material, with the mounting body 22 being defined as the portion of the sheet that is coextensively affixed to the main body 10 and with the retention strap members 20 connected to the mounting body 22 along fold lines 30 so as to be non-adhered to and freely repositionable relative to the main body 10.

Fold lines 30 are defined by the junction of the affixed mounting body 22 and the retention strap members 20. The fold lines 30 are non-parallel and non-perpendicular to both the longitudinal axis 90 and the transverse axis 91, and in this embodiment, meet on the transverse axis 91 at the end of the slit 25. Each fold line 30 is associated with a single retention strap member 20 and defines the attached base 26 of each retention strap member 20. In this manner, the fold lines 30 combine to define an angle facing away from the free ends 21 of the retention strap members 20 in the unfolded configuration substantially less than 180 degrees, preferably an obtuse angle, and most preferably an angle between approximately 110 and 130 degrees. This angle is formed in certain embodiments where the fold lines 30 contact each other, and in other embodiments is formed by extension of the fold lines 30 to an imaginary intersection. In alternative terminology, each fold line 30 extends across a retention strap member 20 such that the inside edge 28 of each retention strap member 20, as defined in this embodiment by slit 25, is shorter than the outside edge 29 of each retention strap member 20, the fold line 30 being non-perpendicular to the inside edge 28 and outside edge 29 at the base 26 of each retention strap member 20. The combination of the fold line 30 and the shorter inside edge 28 of each retention strap member 20 defines an obtuse angle and the combination of the fold line 30 and the outside edge 29 of each retention strap member 20 defines an acute angle.

When folded across the catheter 100, the presence of the angled fold lines 30 eliminate the distortion which occurs when retention straps of known catheter securement devices having fold lines that are perpendicular to the retention straps and the transverse axis are folded across the catheter, the embodiments of the invention thereby providing a more secure restraint.

The upper surface, i.e., the surface facing away from the main body 10, of the mounting body 22 and the upper surface of the unfolded retention strap members 20 are provided with a biocompatible, preferably anti-microbial, adhesive layer or coating 24 of a type capable of adhering to the catheter 100 and to the skin of the patient 103. Prior to using the catheter securement device, the underside of the main body 10 and the upper side of the mounting body 22 and retention strap members 20 are covered with removable release liners (not shown), which are easily removed when the device is to be affixed to the patient's skin 103 and the catheter 100 is to be retained by the retention strap members 20.

Figure 5:
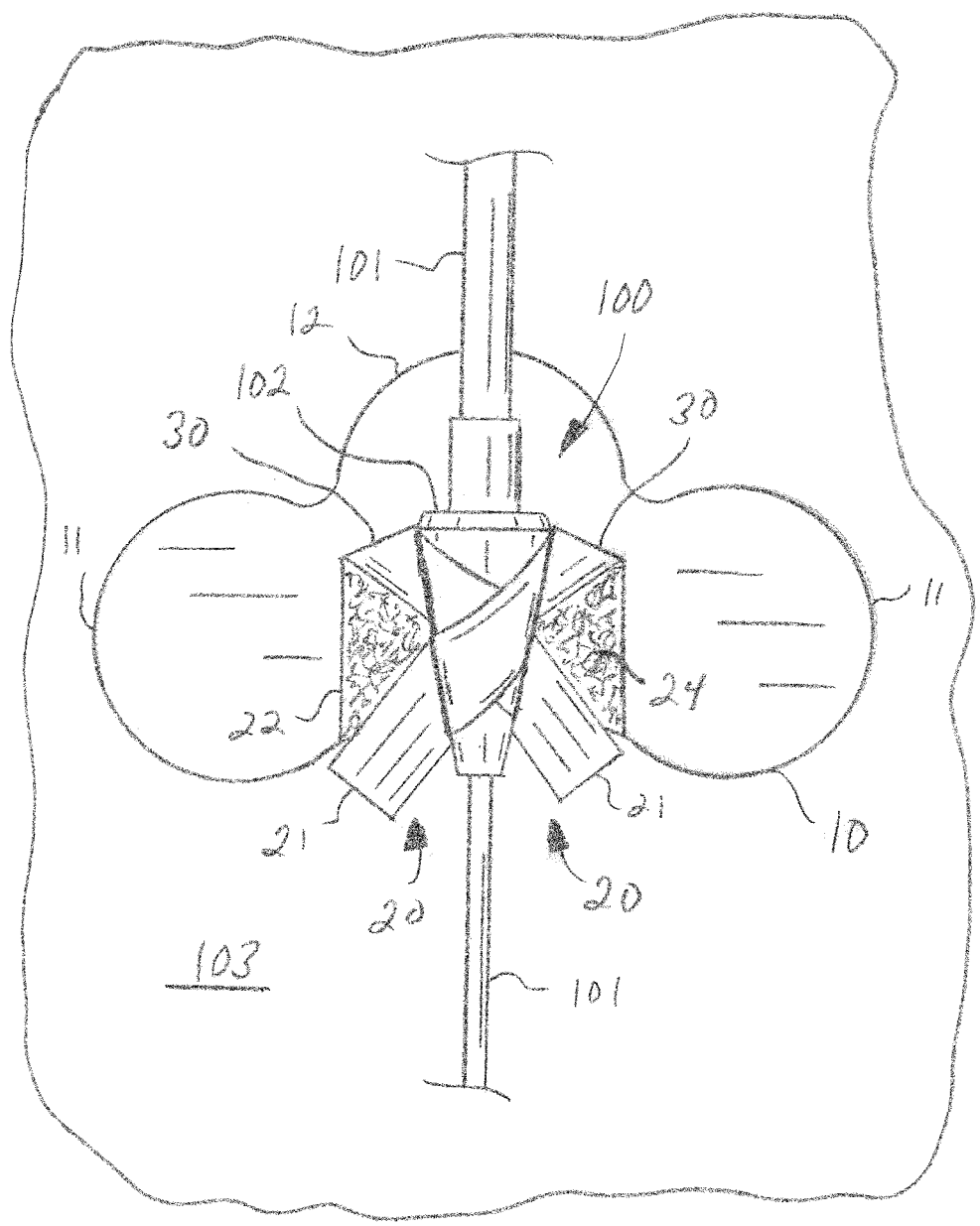
FIG. 5 is an illustration of the embodiment of FIG. 3, shown securing a catheter in place on a patient.
Figure 6:
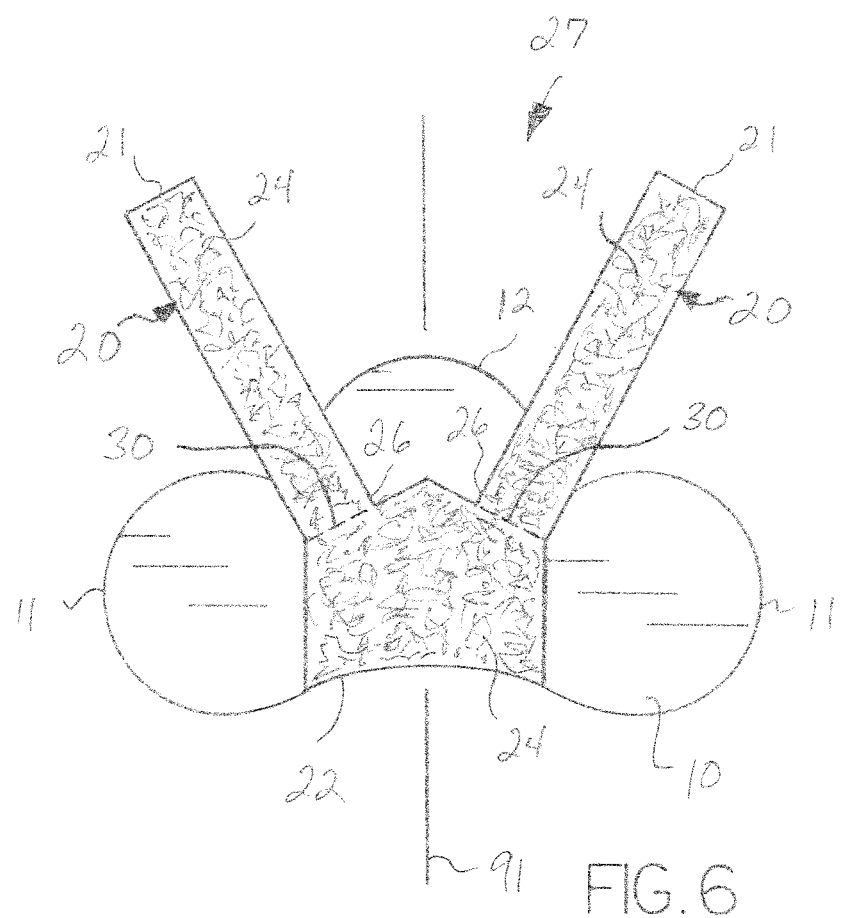
FIG. 6 is an illustration of another embodiment of the catheter securement device, wherein the retention strap members are non-parallel.

As shown in FIGS. 2 and 5, the design and structure of the catheter securement device is such that each of the retention strap members 20 may be folded back toward the mounting body 22 along its fold line 30, which results in the retention strap members 20 extending at an angle across the transverse axis 91, such that one retention strap member 20 will overlap the other, and both retention strap members 20 will overlap the catheter 100. When a catheter 100 is positioned across the mounting body 22 along the transverse axis 91, the underside of the catheter 100 adheres to the exposed adhesive layer 24 of the mounting body 22. To further secure the catheter 100, the free end 21 of a first retention strap member 20 is folded back and angled across the catheter 100, and then the free end 21 of the other retention strap member 20 is folded back and angled across the first retention strap member 20 and the catheter, such that the adhesive layer 24 on the retention strap members 20 is now facing toward the catheter, the mounting body 22 and the patient's skin 103. In this manner, the first retention strap member 20 adheres to the catheter 100, main body 10, mounting body 22 and/or the skin 103 of the patient on one side of the catheter 100, and the second retention strap member 20 adheres to the catheter 100, a portion of the first retention strap member 20, the main body 10, mounting body 22, and/or the skin 103 of the patient on the other side of the catheter 100, thereby forming a chevron-shaped or X-shaped configuration.

In an alternative embodiment shown in FIG. 3, the retention strap members 20 are separated by a gap 27 rather than a slit, the gap 27 defining the shorter inside edge 28 and longer outside edge 29 of each retention strap member 20. As before, the fold lines 30 are angled such that the retention strap members 20 fold across the transverse axis 91 and overlap. In this embodiment as shown, a transverse extension 12 may be provided to increase the dimension of the main body 10 in the transverse direction. The structure of this embodiment is more optimal when securing large, multi-lumen or odd-shaped catheters 100. As in the first embodiment, extension of the fold lines 30 toward the transverse axis 91 combine to define an angle facing away from the free ends 21 of the retention strap members 20 in the unfolded configuration substantially less than 180 degrees, preferably an obtuse angle, and most preferably an angle between approximately 110 and 130 degrees. In alternative terminology, each fold line 30 extends across a retention strap member 20 such that the inside edge 28 of each retention strap member 20, as defined in this embodiment by gap 27, is shorter than the outside edge 29 of each retention strap member 20, the fold line 30 being non-perpendicular to the inside edge 28 and outside edge 29 at the base 26 of each retention strap member 20. The combination of the fold line 30 and the shorter inside edge 28 of each retention strap member 20 defines an obtuse angle and the combination of the fold line 30 and the outside edge 29 of each retention strap member 20 defines an acute angle.

FIG. 6 shows an alternate embodiment similar to FIG. 3 wherein the retention strap members 30 are separated by a gap 27, but wherein the retention strap members 30 are disposed in a V-shaped configuration rather than being parallel or substantially parallel to each other.

Figure 4:
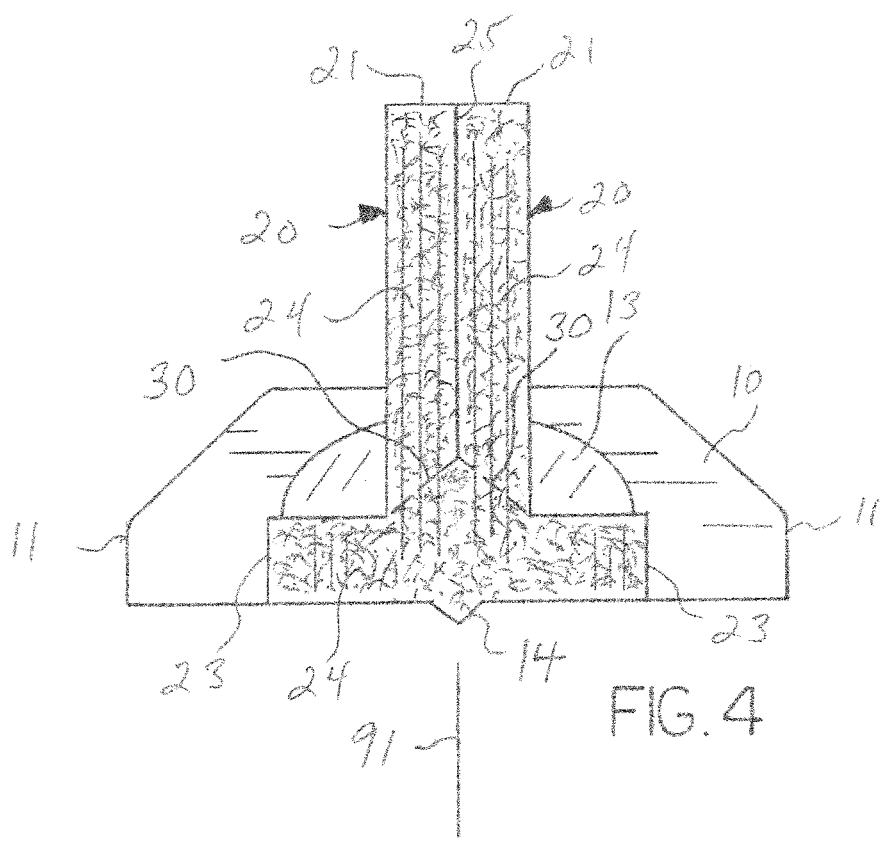
FIG. 4 is an illustration of a third embodiment of the catheter securement device, wherein the mounting base extends beyond the combined width of the two retention strap members.

Still another embodiment is shown in FIG. 4, wherein the mounting body 22 is provided with longitudinal extensions 23. This embodiment also illustrates the provision of a transparent dressing material or window 13, preferably anti-microbial, within the main body 10 to provide visibility to the skin beneath the main body 10.

The structure and design of the catheter securement devices as described and shown increases the security of the catheter 100, as the underside of the catheter 100 is adhered to the adhesive surface 24 of the mounting body 22, which is affixed over a wide surface area of the main body 10, while the sides and top of the catheter 100 are adhered to the adhesive surfaces 24 of the two retention strap members 20, which overlap across the catheter 100, with the free ends 21 of the retention strap members 20 further adhered to the skin 103 of the patient. Thus, excessive movement of the catheter 100 in any direction is prevented and with the layers of adhesives between the catheter and skin, the potential for pressure sores is eliminated. Removal of the catheter 100 is easily accomplished by peeling back both retentions strap members 20 in the opposite order in which they were applied, which can be re-used to secure a replacement catheter 100. Removal of the entire catheter securement device is readily accomplished by peeling the main body 10 from the skin 103 of the patient.

The catheter securement device having the structure set forth above is advantageous from a manufacturing point of view, as the structure enables the retention strap members 20 and the mounting body 22 to be cut or stamped from a single sheet of material, since the retention strap members 20 do not overlap in the unfolded state.

It is understood that equivalents and substitutions for certain elements and structures set forth above may be obvious to those of skill in the art, and therefore the true scope and definition of the invention is to be as set forth in the following claims.

I claim:

1. A catheter securement device comprising a main body, a mounting body affixed to said main body, and retention strap members in an unfolded configuration extending from said mounting body;
    said main body having an upper side and an adhesive underside, said main body defining a transverse axis and a longitudinal axis perpendicular to said transverse axis, said transverse axis being disposed between said retention strap members;
    said retention strap members each having a free end;
    said mounting body being affixed onto said upper side of said main body; said mounting body and said retention strap members having adhesive upper surfaces;
    whereby the junction of each of said retention strap members with said mounting body defines a fold line, such that said fold line is non-parallel and non-perpendicular to both said transverse axis and said longitudinal axis and wherein the combination of said fold lines define an angle facing away from said free ends of said retention strap members in the unfolded configuration of less than 180 degrees;
    whereby said retention straps are structured such that with a catheter positioned on said mounting body along said transverse axis and said retention strap members folded toward said mounting body along said fold lines, said retention strap members are sized and angled to extend across said transverse axis, across the catheter, across each other, and beyond said main body on opposite sides of the catheter.

2. The device of claim 1, wherein said retention strap members are separated by a slit.

3. The device of claim 1, wherein said retention strap members are separated by a gap.

4. The device of claim 1, wherein said retention strap members extend substantially parallel to each other and to said transverse axis in the unfolded state.

5. The device of claim 1, wherein the combination of said fold lines define an obtuse angle facing away from said free ends of said retention strap members in the unfolded configuration.

6. The device of claim 1, wherein the combination of said fold lines define an angle facing away from said free ends of said retention strap members in the unfolded configuration between approximately 110 and 130 degrees.

7. The device of claim 1, wherein said main body further comprises a transverse extension.

8. The device of claim 1, wherein said main body further comprises an alignment guide member.

9. A catheter securement device comprising a main body, a mounting body affixed to said main body, and retention strap members extending from said mounting body;
    said main body having an adhesive underside, said main body defining a transverse axis and a longitudinal axis perpendicular to said transverse axis;
    said retention strap members extending substantially parallel to each other and to said transverse axis in an unfolded state, with said transverse axis disposed between said retention strap members, each said retention strap member having a free end, an inside edge and an outside edge, wherein for each said retention strap member, said inside edge is shorter than said outside edge;
    said mounting body being affixed onto said upper side of said main body; said mounting body and said retention strap members having adhesive upper surfaces;
    whereby the junction of each of said retention strap members with said mounting body defines a fold line, such that each said fold line is non-perpendicular to said inside edge and said outside edge of each retention strap member;
    whereby said retention straps are structured such that with a catheter positioned on said mounting body along said transverse axis and said retention strap members folded toward said mounting body along said fold lines, said retention strap members are sized and angled to extend across said transverse axis, across the catheter, across each other, and beyond said main body on opposite sides of the catheter.

10. The device of claim 9, wherein said retention strap members are separated by a slit.

11. The device of claim 9, wherein said retention strap members are separated by a gap.

12. The device of claim 9, wherein the combination of said fold lines define an angle facing away from said free ends of said retention strap members in the unfolded configuration of less than 180 degrees.

13. The device of claim 9, wherein the combination of said fold lines define an obtuse angle facing away from said free ends of said retention strap members in the unfolded configuration.

14. The device of claim 9, wherein the combination of said fold lines define an angle facing away from said free ends of said retention strap members in the unfolded configuration between approximately 110 and 130 degrees.

15. A catheter securement device comprising a main body, a mounting body affixed to said main body, and retention strap members extending from said mounting body;
    said main body having an adhesive underside, said main body defining a transverse axis and a longitudinal axis perpendicular to said transverse axis;
    said retention strap members extending substantially parallel to each other and to said transverse axis in an unfolded state, with said transverse axis disposed between said retention strap members, each said retention strap member having a free end, an inside edge and an outside edge, wherein for each said retention strap member, said inside edge is shorter than said outside edge;
    said mounting body being affixed onto said upper side of said main body; said mounting body and said retention strap members having adhesive upper surfaces;
    whereby the junction of each of said retention strap members with said mounting body defines a fold line, such that the combination of each said fold line and said shorter inside edge of each said retention strap member defines an obtuse angle and the combination of each said fold line and said outside edge of each retention strap member defines an acute angle;

whereby said retention straps are structured such that with a catheter positioned on said mounting body along said transverse axis and said retention strap members folded toward said mounting body along said fold lines, said retention strap members are sized and angled to extend across said transverse axis, across the catheter, across each other, and beyond said main body on opposite sides of the catheter.

16. The device of claim 15, wherein said retention strap members are separated by a slit.

17. The device of claim 15, wherein said retention strap members are separated by a gap.

18. The device of claim 15, wherein the combination of said fold lines define an angle facing away from said free ends of said retention strap members in the unfolded configuration of less than 180 degrees.

19. The device of claim 15, wherein the combination of said fold lines define an obtuse angle facing away from said free ends of said retention strap members in the unfolded configuration.

20. The device of claim 15, wherein the combination of said fold lines define an angle facing away from said free ends of said retention strap members in the unfolded configuration between approximately 110 and 130 degrees.

* * * * *